(12) United States Patent
Nyce et al.

(10) Patent No.: US 6,426,330 B1
(45) Date of Patent: Jul. 30, 2002

(54) SATIETY INDUCING COMPOSITION COMPRISING NEUROPEPTIDE Y ANALOGUES AND METHODS OF INDUCING SATIETY AND TREATING A DISEASE OR CONDITION ASSOCIATED WITH IT

(75) Inventors: Jonathan W. Nyce; Sherry Ann Leonard, both of Greenville, NC (US)

(73) Assignee: East Carolina University, Greenville, NC (US)

(*) Notice: Subject to any disclaimer, the term of this patent is extended or adjusted under 35 U.S.C. 154(b) by 0 days.

(21) Appl. No.: 09/247,755

(22) Filed: Feb. 9, 1999

Related U.S. Application Data

(62) Division of application No. 08/422,839, filed on Apr. 17, 1995, now Pat. No. 6,075,009.

(51) Int. Cl.[7] .......................... A61K 38/00; C07K 5/00; C07K 7/00
(52) U.S. Cl. .............. 514/15; 514/12; 514/14; 530/300; 530/324; 530/326; 530/328; 424/185.1; 424/400
(58) Field of Search ............. 514/12, 14, 15; 530/300, 324, 326, 328; 424/400, 185.1

(56) References Cited

U.S. PATENT DOCUMENTS 5,026,685 A * 6/1991 Boublik et al. ............ 514/13
5,328,899 A * 7/1994 Boublik et al. ............ 514/13
6,075,009 A * 6/2000 Nyce et al. ................ 514/14

OTHER PUBLICATIONS

K. Tatemoto, *Ann. N.Y. Acad. Sci.* vol. 611, pp. 1–6, 1990.*
K. Tatemoto; Neuropeptide Y: Complete amino acid sequence of the brain peptide. *Proc. Natl. Acad. Sci. USA* 79: 5485–5489 (1992).
K. Tatemoto; Neuropeptide Y and Its Receptor Antagonists. *Ann. NY Acad. Sci* 611:1–6 (1990).
K. Tatemoto et al.; Synthesis of receptor antagonists of neuropeptide Y. *Proc. Natl. Acad. Sci. USA* 89:1174–1178 (1992).

* cited by examiner

*Primary Examiner*—Avis M. Davenport
(74) *Attorney, Agent, or Firm*—Viviana Amzel

(57) ABSTRACT

Satiety inducing composition comprises Neuropeptide Y analogues which are effective for inducing satiety and for treating diseases and conditions associated with a lacking of, or having lowered, satiety.

73 Claims, No Drawings

SATIETY INDUCING COMPOSITION COMPRISING NEUROPEPTIDE Y ANALOGUES AND METHODS OF INDUCING SATIETY AND TREATING A DISEASE OR CONDITION ASSOCIATED WITH IT

PRIOR PATENT APPLICATIONS

This is a divisional application of U.S. patent application Ser. No. 08/422,839, filed Apr. 17, 1995, by the same inventors, and now U.S. Pat. No. 6,075,009.

This invention was made with Government support under Grant No. RO1 CA47217-06 from the National Cancer Institute. The Government may have certain rights in this invention.

BACKGROUND OF THE INVENTION

1. Field of the Invention

The present invention concerns novel Neuropeptide Y analogs, pharmaceutical formulations containing the same and methods of lowering blood pressure and inducing satiety in a subject employing the same.

2. Description of the Background

Neuropeptide Y is a 36 amino acid member of the pancreated polypeptide family. It is highly concentrated in both the central and peripheral mammalian nervous system. It apparently serves important functions in the control of blood pressure, satiety, and other responses. The amino acid sequence of Neuropeptide Y is known. See, e.g., K. Tatemoto, *Proc. Natl. Acad. Sci. USA* 79, 5485–5489 (1982).

Neuropeptide Y analogs are disclosed in U.S. Pat. No. 5,026,685 to Boublik et al. The compounds are indicated to be active in lowering the blood pressure of mammalian subjects. The compounds are indicated to be 18–20 amino acids in length, and include amino acid residues 19 to 36 of human NPY (see, e.g., Column 2, lines 25–35 therein). Additional Neuropeptide Y analogs are disclosed in U.S. Pat. No. 5,328,899 to Boublik et al.

A recent study proposed two modified fragments of NPY, called $PYX_1$ and $PYX_2$, to be specific NPY receptor antagonists. Both compounds are analogs of the 27–36 residue C-terminal fragment. Both compounds have a D-amino acid substitution at $Thr^{32}$. [3-(2,6-dichlorobenzyl)] is substituted at $Tyr^{27}$ on $PYX_1$, and is substituted at both $Tyr^{27}$ and $Tyr^{36}$ in $PYX_2$. See K. Tatemoto, *Ann. NY Acad. Sci.* 611, 1–6 (1990); K. Tatemoto et al., *Proc. Natl. Acad. Sci. USA* 89, 1174–1178 (1992).

SUMMARY OF THE INVENTION

The present invention is based on the a new group of Neuropeptide Y analogs. Active Neuropeptide Y (NPY) analogs. The compounds preferably include amino acids 28–35 of human NPY, and include a D-Thr amino acid substitution at the $Thr^{32}$ position.

The present invention relates to a method of lowering blood pressure in a subject in need of such treatment by administering to the subject the active compounds given above in an amount effective to lower blood pressure.

The present invention relates to a method of inducing satiety in a subject in need of such treatment by administering to the subject the active compounds given above in an amount effective to induce satiety.

The present invention relates to a pharmaceutical formulation comprising the active compounds given above in combination with a pharmaceutically acceptable carrier. The active compound maybe included in the formulation in a pharmaceutically effective amount i.e., an amount effective to lower blood pressure; an amount effective to induce satiety.

The invention also applies the active compounds given above to the preparation of a medicament for lowering blood pressure in a mammalian subject, or for inducing satiety in a mammalian subject.

The foregoing and other objects and aspects of the present invention are explained in detail in the specification set forth hereinbelow.

DESCRIPTION OF THE PREFERRED EMBODIMENTS

The amino acid sequences disclosed herein are presented in the amino to carboxy direction, from left to right. Where the amino acid residue has isomeric forms, it is the L-form of the amino acid that is represented, unless otherwise indicated.

The methods of the present invention are concerned primarily with the treatment of human subjects, but may also be employed for the treatment of other mammalian subjects, such as dogs, cats and cows, for veterinary purposes. Subjects may be those subjects in need of such treatment for any reason for which lowering of blood pressure would be of therapeutic benefit, including but not limited to those subjects afflicted with hypertension or high blood pressure.

The active compounds of the present invention are, in general, NPY analogs that are NPY fragments. The compounds preferably include amino acids 28–35 of NPY, and include a D-Thr amino acid substitution at the $Thr^{32}$ position. The compounds are preferably at least 8, 9 or 10 amino acids in length, and are preferably not more than 15, 16, 17 or 18 amino acids in-length.

Specific examples of active compounds of the present invention are as follows:

| | |
|---|---|
| I: D-Tyr-Ile-Asn-Leu-Ile-D-Thr-Arg-Gln-Arg-D-Tyr-NH$_2$ | (SEQ ID NO:1); |
| I$^{Ac}$: Ac-D-Tyr-Ile-Asn-Leu-Ile-D-Thr-Arg-Gln-Arg-D-Tyr-NH$_2$ | (SEQ ID NO:2); |
| IIB: D-Asp-Pro-Lys-Ser-Pro-Tyr-Ile-Asn-Leu-Ile-D-Thr-Arg-Gln-Arg-D-Tyr-NH$_2$ | (SEQ ID NO:3); |
| IIB$^{Ac}$: Ac-D-Asp-Pro-Lys-Ser-Pro-Tyr-Ile-Asn-Leu-Ile-D-Thr-Arg-Gln-Arg-D-Tyr-NH$_2$ | (SEQ ID NO:4); |
| III: D-Phe(NO$_2$)-Ile-Asn-Leu-Ile-D-Thr-Arg-Gln-Arg-D-Phe(NO$_2$)-NH$_2$ | (SEQ ID NO:5); |
| III$^{Ac}$: Ac-D-Phe(NO$_2$)-Ile-Asn-Leu-Ile-D-Thr-Arg-Gln-Arg-D-Phe(NO$_2$)-NH$_2$ | (SEQ ID NO:6); |
| IV: D-Phe(pF)-Ile-Asn-Leu-Ile-D-Thr-Arg-Gln-Arg-D-Phe(pF)-NH$_2$ | (SEQ ID NO:7); |
| IV$^{Ac}$: Ac-D-Phe(pF)-Ile-Asn-Leu-Ile-D-Thr-Arg-Gln-Arg-D-Phe(pF)-NH$_2$ | (SEQ ID NO:8); |
| V: D-Phe(pCl)-Ile-Asn-Leu-Ile-D-Thr-Arg-Gln-Arg-D-Phe(pCl)-NH$_2$ | (SEQ ID NO:9); |
| V$^{Ac}$: Ac-D-Phe(pCl)-Ile-Asn-Leu-Ile-D-Thr-Arg-Gln-Arg-D-Phe(pCl)-NH$_2$ | (SEQ ID NO:10); |
| VI: D-Phg-Ile-Asn-Leu-Ile-D-Thr-Arg-Gln-Arg-D-Phg-NH$_2$ | (SEQ ID NO:11); | and

| | |
|---|---|
| VI$^{Ac}$: D-Phg-Ile-Asn-Leu-Ile-D-Thr-Arg-Gln-Arg-D-Phg-NH$_2$ | (SEQ ID NO:12). |

The terms used herein have their standard meanings. The term "Ac" means acetyl; the term "Phe(NO$_2$)" refers to phenylalanine substituted by —NO$_2$ on the phenylalanine ring, preferably at the para position, the term "Phe(pCl)" refers to phenylalanine substituted by —Cl on the phenylalanine ring at the para position, and the term "Phe(pF)" refers to phenylalanine substituted by —F on the phenylalanine ring at the para position.

The compounds of the invention may be prepared in accordance with known techniques, such as solid phase-chemistry. See, e.g., U.S. Pat. No. 4,415,558 to Vale et al.

The active compounds disclosed herein may be prepared in the form of their pharmaceutically acceptable salts. Pharmaceutically acceptable salts are salts that retain the desired biological activity of the parent compound and do not impart undesired toxicological effects. Examples of such salts are (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; (b) salts formed from elemental anions such as chlorine, bromine, and iodine, and (c) salts derived from bases, such as ammonium salts, alkali metal salts such as those of sodium and potassium, alkaline earth metal salts such as those of calcium and magnesium, and salts with organic bases such as dicyclohexylamine and N-methyl-D-glucamine.

Pharmaceutical compositions for use in the present method of lowering blood pressure include those suitable for inhalation, oral, rectal, topical, (including buccal, sublingual, dermal and intraocular) parenteral (including subcutaneous, intradermal, intramuscular, intravenous and intraarticular) and transdermal administration. The compositions may conveniently be presented in unit dosage form and may be prepared by any of the methods well known in the art. The formulations may conveniently be presented in unit dosage form and may be prepared.by any of the methods well known in the art.

The dose of active compound administered will vary according to the route of administration, the manner of formulation, the condition of the subject, and the dose at which adverse pharmacological effects occur. One skilled in the art will take such factors into account when determining dosage. In general, in one preferred embodiment, the dosage will be from 400 or 500 up to about 1000, 2000, or 4000 nM/kg subject body weight.

In the manufacture of a medicament according to the invention (a "formulation"), active agents or the physiologically acceptable salts thereof (the "active compound") are typically admixed with, among other things, an acceptable carrier. The carrier must be acceptable in the sense of being compatible with any other ingredients in the formulation and must not be deleterious to the patient. The carrier may be a solid or a liquid, or both, and is preferably formulated with the compound as a unit-dose formulation, for example, a tablet, which may contain from 0.5% to 99% by weight of the active compound. One or more active compounds may be incorporated in the formulations of the invention (e.g., the formulation may contain one or more additional anti-tubercular agents as noted above), which formulations may be prepared by any of the well known techniques of pharmacy consisting essentially of admixing the components, optionally including one or more accessory therapeutic ingredients.

Formulations suitable for oral administration may be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the active compound and a suitable carrier (which may contain one or more accessory ingredients as noted above). In general, the formulations of the invention are prepared by uniformly and intimately admixing the active compound with a liquid or finely divided solid carrier, or both, and then, if necessary, shaping the resulting mixture. For example, a tablet may be prepared by compressing or molding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder. Formulations for oral administration may optionally include enteric coatings known in the art to prevent degradation of the formulation in the stomach and provide release of the drug in the small intestine.

Formulations suitable for buccal (sub-lingual) administration include lozenges comprising the active compound in a flavored base, usually sucrose and acacia or tragacanth; and pastilles comprising the compound in an inert base such as gelatin and glycerin or sucrose and acacia.

Formulations of the present invention suitable for parenteral administration comprise sterile aqueous and non-aqueous injection solutions of the active compound, which preparations are preferably isotonic with the blood of the intended recipient. These preparations may contain anti-oxidants, buffers, bacteriostats and solutes which render the formulation isotonic with the blood of the intended recipient. Aqueous and non-aqueous sterile suspensions may include suspending agents and thickening agents. The formulations may be presented in unit/dose or multi-dose containers, for example sealed ampoules and vials, and may be stored in a freeze-dried (lyophilized) condition requiring only the addition of the sterile liquid carrier, for example, saline or water-for-injection immediately prior to use. Extemporaneous injection solutions and suspensions may be prepared from sterile powders, granules and tablets of the kind previously described.

Formulations suitable for rectal administration are preferably presented as unit dose suppositories. These may be prepared by admixing the active compound with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which may be used include vaseline, lanoline, polyethylene glycols, alcohols, transdermal enhancers, and combinations of two or more thereof.

Formulations suitable for transdermal administration may be presented as discrete patches adapted to remain in intimate contact with the epidermis of the recipient for a prolonged period of time. Formulations suitable for transdermal administration may also be delivered by iontophoresis (see, e.g., *Pharmaceutical Research* 3, 318 (1986)) and typically take the form of an optionally buffered aqueous solution of the active compound.

The following examples are provided to more fully illustrate the present invention and should not be construed as restrictive thereof. In the following examples, temperatures are given in degrees centigrade unless otherwise indicated.

EXAMPLES

Example 1
Synthesis of NPY27-36 (D-Tyr$^{27,36}$, D-Thr$^{32}$)

NPY27-36 (D-Tyr$^{27,36}$, D-Thr$^{32}$) was synthesized using Fmoc-BOP chemistry in accordance with known techniques. The automated BIOSEARCH model 9600 peptide synthesizer was used to produce the peptide. The amino acid derivatives were Arg (Mtr), Ile, Leu, Thr (tBu), tYR (tBu), Asn (Tmob) and Gln (Tmob). Tyr$^{27}$, Thr$^{32}$ and Tyr$^{36}$ were D isomers. To remove the side chain protecting group and separate the pepetide from the resin (PAL resin), TFA/thioanisol/ethanedithiol/anisol was used in molar excess (10 ml/g). After deprotection of the final product, the peptide was purified over a 2"×25 cm VYDAC 15–20 micron C$_{18}$ column using a Waters model 600-E HPLC with 0.1% TFA and 60% acetonitrile in 0.1% TFA applying a linear gradient over 45 minutes. The primary peak detected by UV absorbance at 215 nm was collected and repeatedly lyophilized. The purity of the end product, having the sequence D-Tyr-Ile-Asn-Leu-Ile-D-Thr-Arg-Gln-Arg-D-Tyr-NH$_2$ (SEQ ID NO:1) (M.W. 1336.57), was ≧95%.

Example 2
Synthesis of Additional NPY Analogs

The following compounds were synthesized in essentially the same manner as given in Example 1 above to yield the indicated compounds:

I$^{Ac}$: Ac-D-Tyr-Ile-Asn-Leu-Ile-D-Thr-Arg-
    Gln-Arg-D-Tyr-NH$_2$     (SEQ ID NO:2) (M.W. 1378.62);

IIB: D-Asp-Pro-Lys-Ser-Pro-Tyr-Ile-Asn-Leu-
    Ile-D-Thr-Arg-Gln-Arg-D-Tyr-(SEQ ID NO:3) (M.W. 1864.14);

IIB$^{Ac}$: Ac-D-Asp-Pro-Lys-Ser-Pro-Tyr-Ile-Asn-
    Leu-Ile-D-Thr-Arg-Gln-Arg-D-(SEQ ID NO:4) (M.W. 1906.19);

III: D-Phe(NO$_2$)-Ile-Asn-Leu-Ile-D-Thr-Arg-Gln-
    Arg-D-Phe(NO$_2$)-NH$_2$     (SEQ ID NO:5) (M.W. 1396.58);

III$^{Ac}$: Ac-D-Phe(NO$_2$)-Ile-Asn-Leu-Ile-D-Thr-Arg-
    Gln-Arg-D-Phe(NO$_2$)-NH$_2$     (SEQ ID NO:6)(M.W. 1438.63);

IV: D-Phe(pF)-Ile-Asn-Leu-Ile-D-Thr-Arg-Gln-
    Arg-D-Phe(pF)-NH$_2$     (SEQ ID NO:7) (M.W. 1342.57);

IV$^{Ac}$: Ac-D-Phe(pF)-Ile-Asn-Leu-Ile-D-Thr-Arg-
    Gln-Arg-D-Phe(pF)-NH$_2$     (SEQ ID NO:8) (M.W. 1342.57);

V: D-Phe(pCl)-Ile-Asn-Leu-Ile-D-Thr-Arg-Gln-
    Arg-D-Phe(pCl)-NH$_2$     (SEQ ID NO:9) (M.W. 1359.02);

V$^{Ac}$: Ac-D-Phe(pCl)-Ile-Asn-Leu-Ile-D-Thr-Arg-
    Gln-Arg-D-Phe(pCl)-NH$_2$     (SEQ ID NO:10) (M.W. 1401.07);

VI: D-Phg-Ile-Asn-Leu-Ile-D-Thr-Arg-Gln-Arg-
    D-Phg-NH$_2$     (SEQ ID NO:11) (M.W. 1306.54);

and

VI$^{Ac}$: D-Phg-Ile-Asn-Leu-Ile-D-Thr-Arg-Gln-
    Arg-D-Phg-NH$_2$     (SEQ ID NO:12) (M.W. 1348.59).

Example 3
In Vivo Activity of NPY27-36 (D-Tyr$^{27,36}$, D-Thr$^{32}$)

Male Sprague-Dawley rats obtained from Charles River Laboratories, Wilmington, Mass., and weighing 276–300 g, were group housed at 22° C. and kept on 12 hour light/dark cycle. Food and water were provided ad lib.

Animals were anesthetized with sodium pentobarbital (65 mg/kg) and under sterile conditions a one-inch incision was made in the fold of the left leg to expose the femoral blood vessels. Two lengths of PE-50 tubing filled with 10% heparin were inserted into the left femoral artery and left femoral vein for measurement of blood pressure and for drug delivery, respectively. The tubings were tunneled under the skin and exposed through the mid-scapular region. Animals were allowed at least 24 hours recovery prior to experiments.

A force transducer (Spectramed Model P23XL, Grass Instruments, Quincy, Mass., USA), and tachograph (Model 7P44D, Grass Instruments) was used for recording of systolic and diastolic pressures and heart rate from the femoral artery catheter. Patency of catheters was verified by flushing with either saline or 10% heparin.

A dose of either 30, 100, 500, 800 or 1000 nM/kg (nanomoles per liter per kilogram) of NPY27-36 (D-Tyr$^{27,36}$, D-Thr$^{32}$) (prepared as described in Example 1 above), or saline was delivered to the animal via the catheter in the left femoral vein. Changes in systolic and diastolic pressures and heart rater were recorded from the catheter in the left femoral artery over a 10 minute time interval.

NPY27-36 (D-Tyr$^{27,36}$, D-Thr$^{32}$) produced a dose-dependent decrease in mean arterial pressure and an increase in heart rate when given intraveneously to the normotensive Sprague-Dawley rats. Doses of 30 and 100 nM/kg failed to produce changes that were significantly different from saline treatment. When given in doses of 500, 800, and 1000 nM/Kg, however, significantly different decreases in mean arterial pressure were seen ad is as compared to saline-treated controls. Further, doses of 500 and 1000 nM/kg produced significantly different increases in heart rate as compared to saline controls.

The foregoing examples are illustrative of the present invention, and are not to be construed as limiting thereof. The invention is defined by the following claims, with equivalents of the claims to be included therein.

That which is claimed is:

1. A satiety inducing composition, comprising
   a satiety induced amount of a modified Neuropeptide Y having satiety inducing activity and consisting of a fragment of 8 to 18 amino acids of a Neuropeptide Y, which fragment comprises an amino acid segment selected from the group consisting of amino acids 28 to 35 of a Neuropeptide Y, wherein D-Thr is substituted for Thr at position 32, pharmaceutically acceptable salts thereof, and mixtures thereof; and
   a physiologically acceptable carrier.

2. The composition of claim 1, wherein the modified Neuropeptide Y comprises 9 to 17 amino acids.

3. The composition of claim 2, wherein the modified Neuropeptide Y comprises 10 to 16 amino acids.

4. The composition of claim 3, wherein the modified Neuropeptide Y comprises 15 amino acids.

5. The composition of claim 1, wherein the modified Neuropeptide Y is selected from the group consisting of D-Tyr-Ile-Asn-Leu-Ile-D-Thr-Arg-Gln-Arg-
    D-Tyr-NH$_2$     (SEQ ID NO:1);

D-Tyr-Ile-Asn-Leu-Ile-D-Thr-Arg-Gln-Arg-
    D-Tyr-NH$_2$     (SEQ ID NO:2);

D-Asp-Pro-Lys-Ser-Pro-Tyr-Ile-Asn-Leu-Ile-
    D-Thr-Arg-Gln-Arg-D-Tyr-NH$_2$     (SEQ ID No:3);

Ac-D-Asp-Pro-Lys-Ser-Pro-Tyr-Ile-Asn-Leu-
    Ile-D-Thr-Arg-Gln-Arg-D-Tyr-NH2     (SEQ ID No:4);

| | |
|---|---|
| D-Phe(NO2)-Ile-Asn-Leu-Ile-D-Thr-Arg-Gln-Arg-D-Phe(NO2)-NH2 | (SEQ ID NO:5); |
| Ac-D-Phe(NO2)-Ile-Asn-Leu-Ile-D-Thr-Arg-Gln-Arg-D-Phe(NO2)-NH2 | (SEQ ID NO:6); |
| D-Phe(pF)-Ile-Asn-Leu-Ile-D-Thr-Arg-Gln-Arg-D-Phe(pF)-NH2 | (SEQ ID NO:7); |
| Ac-D-Phe(pF)-Ile-Asn-Leu-Ile-D-Thr-Arg-Gln-Arg-D-Phe(pF)-NH2 | (SEQ ID NO:8); |
| D-Phe(pCl)-Ile-Asn-Leu-Ile-D-Thr-Arg-Gln-Arg-D-Phe(pCl)-NH2 | (SEQ ID NO:9); |
| Ac-D-Phe(pCl)-Ile-Asn-Leu-Ile-D-Thr-Arg-Gln-Arg-D-Phe(pCl)-NH2 | (SEQ ID NO:10); |
| D-Phg-Ile-Asn-Leu-Ile-D-Thr-Arg-Gln-Arg-D-Phg-NH2 | (SEQ ID NO:11); | and

| | |
|---|---|
| D-Phg-Ile-Asn-Leu-Ile-D-Thr-Arg-Gln-Arg-D-Phg-NH2 | (SEQ ID NO:12); | wherein Ac represents acetyl, Phe(NO$_2$) represents NO$_2$ substituted phenylalanine, Phe(pCl) represents phenylalanine substituted by Cl on the phenylalanine ring, and Phe(pF) represents phenylalanine substituted by F on the phenylalanine.

6. The composition of claim 5, wherein the modified Neuropeptide Y is freeze-dried or lyophilized.

7. The composition of claim 5, wherein the modified Neuropeptide Y is SEQ. ID NO: 1, a pharmaceutically acceptable salt thereof or mixtures thereof.

8. The composition of claim 5, wherein the modified Neuropeptide Y is SEQ. ID NO: 2, a pharmaceutically acceptable salt thereof or mixtures thereof.

9. The composition of claim 5, wherein the modified Neuropeptide Y is SEQ. ID NO: 3, a pharmaceutically acceptable salt thereof or mixtures thereof.

10. The composition of claim 5, wherein the modified Neuropeptide Y is SEQ. ID NO: 4, a pharmaceutically acceptable salt thereof or mixtures thereof.

11. The composition of claim 5, wherein the modified Neuropeptide Y is SEQ. ID NO: 5, a pharmaceutically acceptable salt thereof or mixtures thereof.

12. The composition of claim 5, wherein the modified Neuropeptide Y is SEQ. ID NO: 6, a pharmaceutically acceptable salt thereof or mixtures thereof.

13. The composition of claim 5, wherein the modified Neuropeptide Y is SEQ. ID NO: 7, a pharmaceutically acceptable salt thereof or mixtures thereof.

14. The composition of claim 5, wherein the modified Neuropeptide Y is SEQ. ID NO: 8, a pharmaceutically acceptable salt thereof or mixtures thereof.

15. The composition of claim 5, wherein the modified Neuropeptide Y is SEQ. ID NO: 9, a pharmaceutically acceptable salt thereof or mixtures thereof.

16. The composition of claim 5, wherein the modified Neuropeptide Y is SEQ. ID NO: 10, a pharmaceutically acceptable salt thereof or mixtures thereof.

17. The composition of claim 5, wherein the modified Neuropeptide Y is SEQ. ID NO: 11, a pharmaceutically acceptable salt thereof or mixtures thereof.

18. The composition of claim 5, wherein the modified Neuropeptide Y is SEQ. ID NO: 12, a pharmaceutically acceptable salt thereof or mixtures thereof.

19. The composition of claim 1, wherein the modified Neuropeptide Y is operatively linked to a Neuropeptide Y-unrelated amino acid segment, a pharmaceutically acceptable salt thereof or mixtures thereof.

20. The composition of claim 1, wherein the carrier is a pharmaceutically acceptable carrier.

21. The composition of claim 1, comprising about 0.5 to about 99% of the modified Neuropeptide Y.

22. The composition of claim 1, wherein the carrier is selected from the group consisting of solid and liquid carriers.

23. The composition of claim 1, which further comprises an agent selected from the group consisting of other therapeutic agents, flavorings, lubricants, suspending and thickening agents, binders, inert diluents, surface active agents, dispersants, antioxidants, buffers, bacteriostats and solutes to attain isotonicity.

24. The composition of claim 23, comprising a therapeutic agent that is a tubercular agent.

25. The composition of claim 1, which is in the form of a formulation selected from the group consisting of inhalable, oral, rectal, topical, parenteral, and transdermal formulations.

26. The formulation of claim 25, which is selected from the group consisting of buccal, sublingual, dermal, intraocular, subcutaneous, intradermal, intramuscular, intravenous, iontophoretic, intraarticular, and transdermal formulations.

27. The formulation of claim 25, which is in a form selected from the group consisting of capsules, cachets, pastilles, lozenges, powder, granules, solution, suspension, emulsion and tablets.

28. The formulation of claim 27, which comprises a suspension or solution in an aqueous or non-aqueous liquid or an oil-in-water or water-in-oil emulsion.

29. The formulation of claim 27, which is in the form of a capsule.

30. The formulation of claim 25, which is an oral formulation.

31. The oral formulation of claim 30, which comprises a solution or suspension selected from the group consisting of aqueous and non-aqueous liquid solutions and suspensions.

32. The oral formulation of claim 30, which comprises an emulsion selected from the group consisting of oil-in-water and water-in-oil emulsions.

33. The oral formulation of claim 30, which further comprises an enteric coating.

34. The formulation of claim 25, which comprises a buccal or sub-lingual formulation selected from the group consisting of lozenges further comprising a flavoring agent selected from the group consisting of sucrose, acacia and tragacanth; and pastilles further comprising an inert base selected from the group consisting of gelatin, glycerin, sucrose and acacia.

35. The formulation of claim 25, which comprises a parenteral formulation.

36. The parenteral formulation of claim 35, which comprises a solution, suspension or emulsion.

37. The parenteral formulation of claim 35, which is an injectable formulation.

38. The injectable formulation of claim 37, which is selected from the group consisting of injectable solutions or suspensions, and which may further comprise an agent selected from the group consisting of antioxidants, buffers, bacteriostatic agents and solutes which render the solution or suspension isotonic with the blood of a recipient.

39. The injectable formulation of claim 38, wherein the solutions and suspensions are selected from the group consisting of sterile aqueous and non-aqueous injection solutions and suspensions, which may further comprise suspending agents and thickening agents.

40. The formulation of claim 25, which is a topical formulation selected from the group consisting of ointments, creams, lotions, pastes, gels, sprays, aerosols and oils; and may further comprise a carrier selected from the group consisting of vaseline, lanoline, polyethylene glycols, alcohols and trans-dermal enhancers.

41. The formulation of claim 25, which is a transdermal formulation.

42. The transdermal formulation of claim 41, which is comprised in a transdermal device.

43. The transdermal formulation of claim 41, which comprises an iontophoretic formulation selected from the group consisting of iontophoretic solutions and suspensions, and which may further comprise a buffer.

44. The transdermal formulation of claim 42, wherein the transdermal device is an iontophoretic device further comprising means for iontophoretic delivery.

45. The composition of claim 23, which is in the form of a sub-lingual formulation, further comprising a flavoring and inert diluent selected from the group consisting of sucrose, acacia, tragacanth, gelatin and glycerin.

46. The formulation of claim 25, which is a rectal formulation.

47. The formulation of claim 25, which is an inhalable formulation.

48. The formulation of claim 25, which is an intraocular formulation.

49. A method of inducing satiety, comprising administering to a subject in need of treatment a satiety inducing amount of the composition of claim 1.

50. The method of claim 49, wherein the composition is administered parenterally.

51. The method of claim 49, wherein the composition is administered orally, intraocularly, or buccally.

52. The method of claim 49, wherein the composition is administered dermally, transdermally, intradermally, intraarticularly, or iontophoretically.

53. The method of claim 49, wherein the composition is administered topically.

54. The method of claim 49, wherein the composition is administered transdermally.

55. The method of claim 49, wherein the composition is administered sub-lingually.

56. The method of claim 49, wherein the composition is administered rectally.

57. The method of claim 49, wherein the composition is administered by means of a transdermal device comprising a patch.

58. The method of claim 49, which is a prophylactic method.

59. The method of claim 49, which is a therapeutic method.

60. The method of claim 49, wherein the composition is administered in an amount of about 400 to about 4000 nmole/kg body weight.

61. The method of claim 49, wherein the subject is human.

62. The method of claim 49, wherein the subject is an animal.

63. A method of treating a disease or condition associated with low, or lack of, satiety, comprising administering to a subject in need of such treatment the method of claim 49, wherein the composition comprises a therapeutically effective amount of the modified Neuropeptide.

64. The method of claim 63, wherein the composition is administered rectally.

65. The method of claim 63, wherein the composition is administered dermally, parenterally, transdermally or intraarticularly.

66. The method of claim 63, wherein the composition is administered by inhalation.

67. The method of claim 63, wherein the composition is administered intraocularly.

68. The method of claim 63, wherein the composition is administered sublingually or orally.

69. The method of claim 63, wherein the composition is administered buccally.

70. The method of claim 63, wherein the composition is administered subcutaneously, intradermally, intramuscularly, intravenously or intraarticularly.

71. The method of claim 63, wherein the composition is administered dermally.

72. The method of claim 63, wherein the composition is administered by means of a patch.

73. The method of claim 63, wherein the composition is administered by iontophoresis.

* * * * *